(12) United States Patent
Viola

(10) Patent No.: US 9,427,271 B2
(45) Date of Patent: Aug. 30, 2016

(54) PERCUTANEOUS EXCHANGE TUBE AND METHOD OF USE

(71) Applicant: OsteoMed LLC, Addison, TX (US)

(72) Inventor: Randall W. Viola, Vail, CO (US)

(73) Assignee: OsteoMed LLC, Addison, TX (US)

( * ) Notice: Subject to any disclaimer, the term of this patent is extended or adjusted under 35 U.S.C. 154(b) by 360 days.

(21) Appl. No.: 14/218,584

(22) Filed: Mar. 18, 2014

(65) Prior Publication Data

US 2015/0265328 A1 Sep. 24, 2015

(51) Int. Cl.
| | |
|---|---|
| *A61B 17/88* | (2006.01) |
| *A61B 17/17* | (2006.01) |
| *A61B 17/56* | (2006.01) |
| *A61B 17/16* | (2006.01) |
| *A61B 17/90* | (2006.01) |
| *A61B 17/34* | (2006.01) |
| *A61B 17/86* | (2006.01) |

(52) U.S. Cl.
CPC ........... *A61B 17/88* (2013.01); *A61B 17/1615* (2013.01); *A61B 17/1686* (2013.01); *A61B 17/17* (2013.01); *A61B 17/1739* (2013.01); *A61B 17/3472* (2013.01); *A61B 17/56* (2013.01); *A61B 17/8872* (2013.01); *A61B 17/8875* (2013.01); *A61B 17/8897* (2013.01); *A61B 17/864* (2013.01); *A61B 2017/1782* (2013.01); *A61B 2017/349* (2013.01); *A61B 2017/564* (2013.01); *A61B 2017/90* (2013.01); *A61B 2090/062* (2016.02)

(58) Field of Classification Search
CPC .............. A61B 17/17; A61B 17/1739; A61B 2017/1782; A61B 17/3472; A61B 2017/349; A61B 17/56; A61B 2017/564; A61B 17/88; A61B 17/8872; A61B 17/8875; A61B 2017/90; B25B 23/04; B25B 23/08; B25B 23/10; B25B 23/101
See application file for complete search history.

(56) References Cited

U.S. PATENT DOCUMENTS

| | | | | |
|---|---|---|---|---|
| 8,425,574 | B2 * | 4/2013 | Huebner | A61B 17/1728 606/281 |
| 2008/0041196 | A1 * | 2/2008 | Companioni | A61B 17/862 81/453 |
| 2009/0036931 | A1 * | 2/2009 | Pech | A61B 17/1725 606/280 |
| 2011/0106086 | A1 * | 5/2011 | Laird | A61B 17/1728 606/70 |
| 2014/0214086 | A1 * | 7/2014 | Benson | A61B 17/1655 606/279 |
| 2014/0243837 | A1 * | 8/2014 | Mebarak | A61B 17/1728 606/96 |

OTHER PUBLICATIONS http://www.osteomed.com/SBO_Upper/Literature/HPS_STG.pdf (last accessed Mar. 18, 2014).
http://www.osteomed.com/SBO_Upper/Literature/HPS_Implants.pdf, pp. 4 and 5 (last accessed Mar. 18, 2014).
http://www.osteomed.com/SBO_lower/Literature/ExtreiLOK_STG.pdf, p. 6 (last accessed Mar. 18, 2014).
http://www.osteomed.com/SBO_Lower/Literature/ExtremiFix_Brochure.pdf, p. 4 (last accessed Mar. 18, 2014).

* cited by examiner

*Primary Examiner* — Larry E Waggle, Jr.
(74) *Attorney, Agent, or Firm* — Norton Rose Fulbright US LLP

(57) ABSTRACT

An improved medical device tube is disclosed for use in a percutaneous procedure. An improved medical procedure is also disclosed to insert a cannulated screw across a fracture of a human bone using the improved tube.

9 Claims, 15 Drawing Sheets

PERCUTANEOUS EXCHANGE TUBE AND METHOD OF USE

TECHNICAL FIELD

The present disclosure relates generally to a medical device used in a percutaneous manner and the related medical procedure.

BACKGROUND

In the installation of cannulated screws and other fasteners in the medical field, the traditional process has been to first identify the target area into which the cannulated screw or other fastener needs to be attached. Once the target area is defined, a guide wire is implanted. Such a guide wire may be a K-wire or equivalent guide wire well known to those skilled in the art. It may be threaded at one end for rotational installation or may be inserted following the drilling of a small pilot hole. Once the preliminary guide wire is installed, a hollow drill bit is placed over the guide wire and drilled into the target area of the bone. The drill is then removed and a cannulated screw placed over the remaining guide wire. The cannulated screw is then rotated into the bone to achieve its intended purpose. Once installed, the guide wire inserted at the beginning of the procedure is unthreaded or otherwise removed.

A problem has arisen from time to time when attempting to remove the hollow drill bit after it has been placed over the guide wire and used to drill a predetermined sized hole for the forthcoming cannulated screw. The problem is that upon removal of the hollow drill bit, the guide wire also comes out of the target site. Since the incision for the initial guide wire is small, the wound site may be lost and the surgeon in the position of having to search for the drill site for placement of a cannulated screw. Such may result in further irritation of the wound site and loss of precision time. Such may also result in a loss of the precise orientation of the initial guide wire which is critical to properly orient the cannulated screw. As a result, the need exists for an improved device and procedure for the insertion of a cannulated screw in the target location of a human bone. The guide wire is small as smaller wires typically are used to place screws ≤3.5 mm in diameter. Thus, it is frequently flimsy and difficult to direct.

BRIEF SUMMARY

The present invention provides for an apparatus and a medical procedure used to install a cannulated screw or other fastener which does not result in the premature removal of the initial guide wire and allows much more accurate placement of the pilot hole for the cannulated screw.

The apparatus may be referred to as a percutaneous tube or exchange tube. It comprises a first elongated hollow portion having first and second ends. The first end is preferably threaded for threadable engagement within the target location of a human bone. The apparatus also includes a second elongated hollow portion, also having a first and second end. The first end of the second elongated portion is attached to the second end of the first elongated portion. As both the first and second elongated portions are hollow, they are aligned such that the longitudinal axis of the first elongated portion is coaxially with the longitudinal axis of the second elongated portion. Furthermore, the inner diameters of both the first elongated hollow portion and the second elongated hollow portion are substantially the same, thereby providing a uniform hollow tube extending from the first end of the first elongated hollow portion through to the second end of the second elongated hollow portion. The outer diameter of the second elongated portion is preferably greater than the outer diameter of the first elongated portion, thereby minimizing the size of the wound that must be made in order to accommodate the threaded end of the first elongated portion while the larger outer diameter of the second elongated portion provides a handle for the surgeon to more easily manipulate and rotate the apparatus.

The improved process using the percutaneous tube comprises a first step of inserting a first or initial guide wire, such as a K-wire, into a target location of a human bone. Once the first guide wire is secured in place, the surgeon places the threaded end of the first elongated hollow portion over the guide wire, lowers it along the guide wire, and then screws the first end of the first elongated hollow portion by means of the threaded end into the bone. The target site is well defined since the first guide wire provides orientation and direction. The first or initial guide wire is then removed and a second guide wire having an outer diameter smaller than the outer diameter of the first guide wire is then inserted through the elongated hollow portions of the apparatus and into the target location of the bone. In this manner, a second guide wire having a smaller diameter than the original guide wire is then available to orient and guide any forthcoming fasteners into the precise location. Once the second guide wire is secured at the target site, the apparatus is unscrewed and removed, leaving the second guide wire within the target location. The second guide wire is small enough so as not to be affected or accidentally removed when the apparatus is unscrewed and removed. Due to its smaller diameter the second guide wire may more easily accommodate the inner diameter of a preselected cannulated screw. The cannulated screw is then lowered over the second guide wire and screwed into the target location of the bone using conventional techniques. The screw has a maximum threaded outer diameter that is greater than the outer diameter of the first guide wire and the outer diameter of the threaded end of the first elongated hollow portion of the tube. In this manner, the outer threaded diameter of the cannulated screw has maximum retention since it is entering bone matter not previously contacted by either the first guide wire, the second guide wire, or the percutaneous tube.

A key purpose of the exchange tube is to facilitate the percutaneous placement of orthopedic screws. In the prior art small wire is first drilled into the target bone. However, these small wires are very difficult to position due to their small diameter. Larger wires cannot be used in the prior art techniques because it is difficult, if not impossible to put cannulated screws over them. As further discussed herein this problem is solved by the exchange tube. The initial pilot hole is drilled with a large wire. The exchange tube is then inserted over the large wire and engaged into the target site of the bore. The large wire is then removed and replaced with a small wire. The exchange tube is then removed and a cannulated screw may be placed.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments.

BRIEF DESCRIPTION OF THE DRAWINGS

For a more complete understanding of the disclosed method and apparatus, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed method and apparatus or which render other details difficult to perceive may have been omitted. It should be understood, of course, that this disclosure is not limited to the particular embodiments illustrated herein.

DETAILED DESCRIPTION

Figure 1:
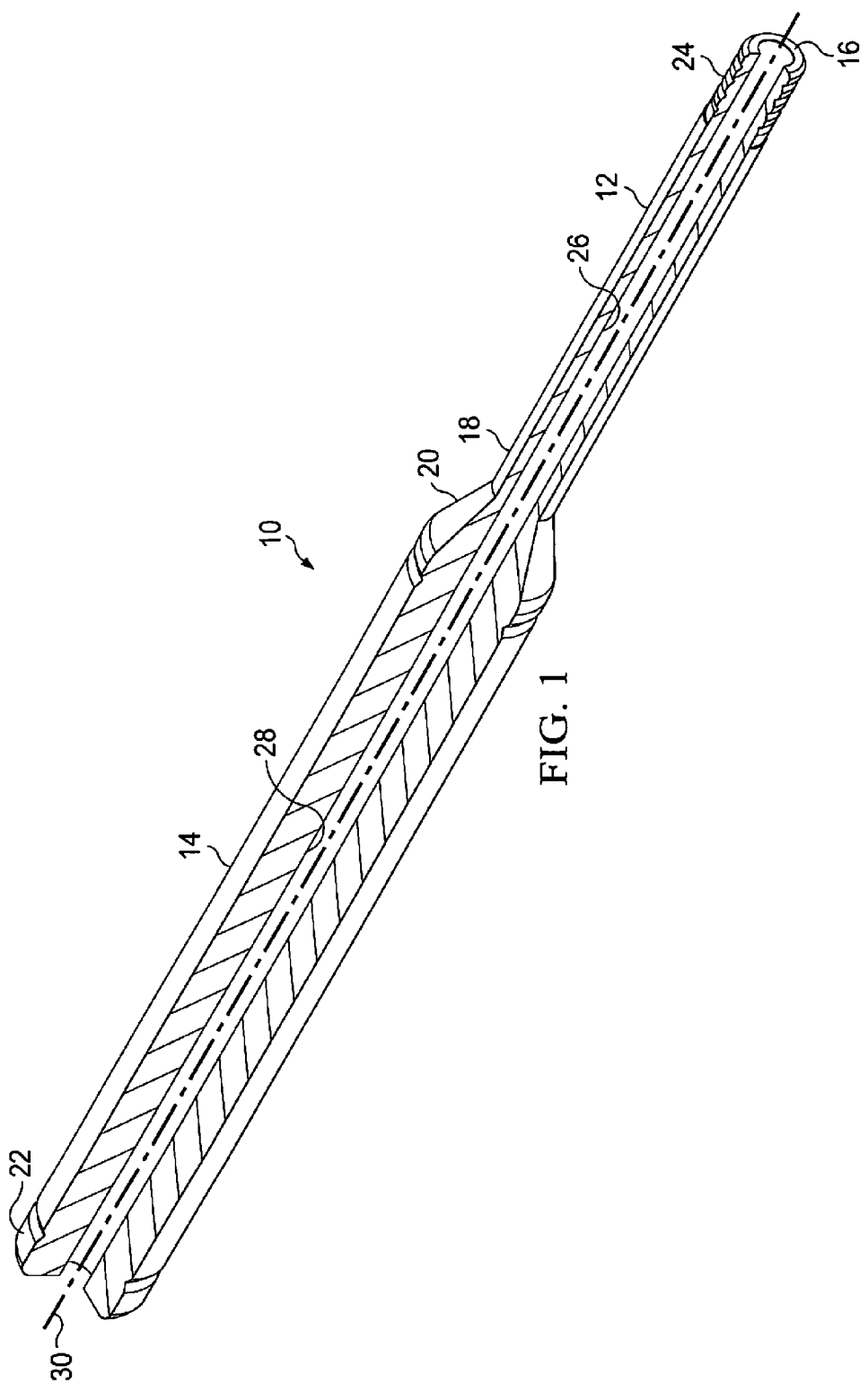
FIG. 1 is an elevation view of the apparatus of the present invention.

Referring to FIG. 1, the apparatus of the present invention, also referred to as a percutaneous exchange tube 10 or exchange tube 10, comprises a first portion 12 and a second portion 14. First portion 12 includes a first end 16 and a second end 18, and second portion 14 includes a first end 20 and a second end 22. First portion 12 is attached or connected to second portion 14. Second portion 14 has a slightly larger outer diameter, permitting the surgeon to more easily grasp the instrument. First end 16 of portion 12 has a threaded portion 24. First portion 12 and second portion 14 each include a hollow elongated section 26 and 28, respectively, which extend along the longitudinal axis 30 of first portion 12 and second portion 14. Once manufactured as a single unit or first and second portions 12 and 14 are attached in a permanent manner, hollow section 26 is coaxially aligned with hollow section 28, providing a uniform inner diameter.

Exchange tube 10 is intended to be held by the surgeon. Once an incision is made to open the target site of the human bone under repair, threaded portion 24 of exchange tube 10 is intended to be screwed into the target site in accordance with the procedures set forth below. Exchange tube 10 is intended to be used in a percutaneous manner. That is, it is intended to be used by the surgeon in a way to minimize the open wound at the target site of the bone under repair in accordance with the procedure of the present invention, thereby minimizing the healing period.

Referring now to FIGS. 2A-2D, the conventional or prior art procedure for installation of a cannulated screw will be discussed. A problem associated with the conventional technique will then be demonstrated and the benefits of the percutaneous exchange tube 10 will be highlighted with respect to the preferred medical procedure of the present invention as set forth in FIGS. 3A-3J.

Figure 2A:
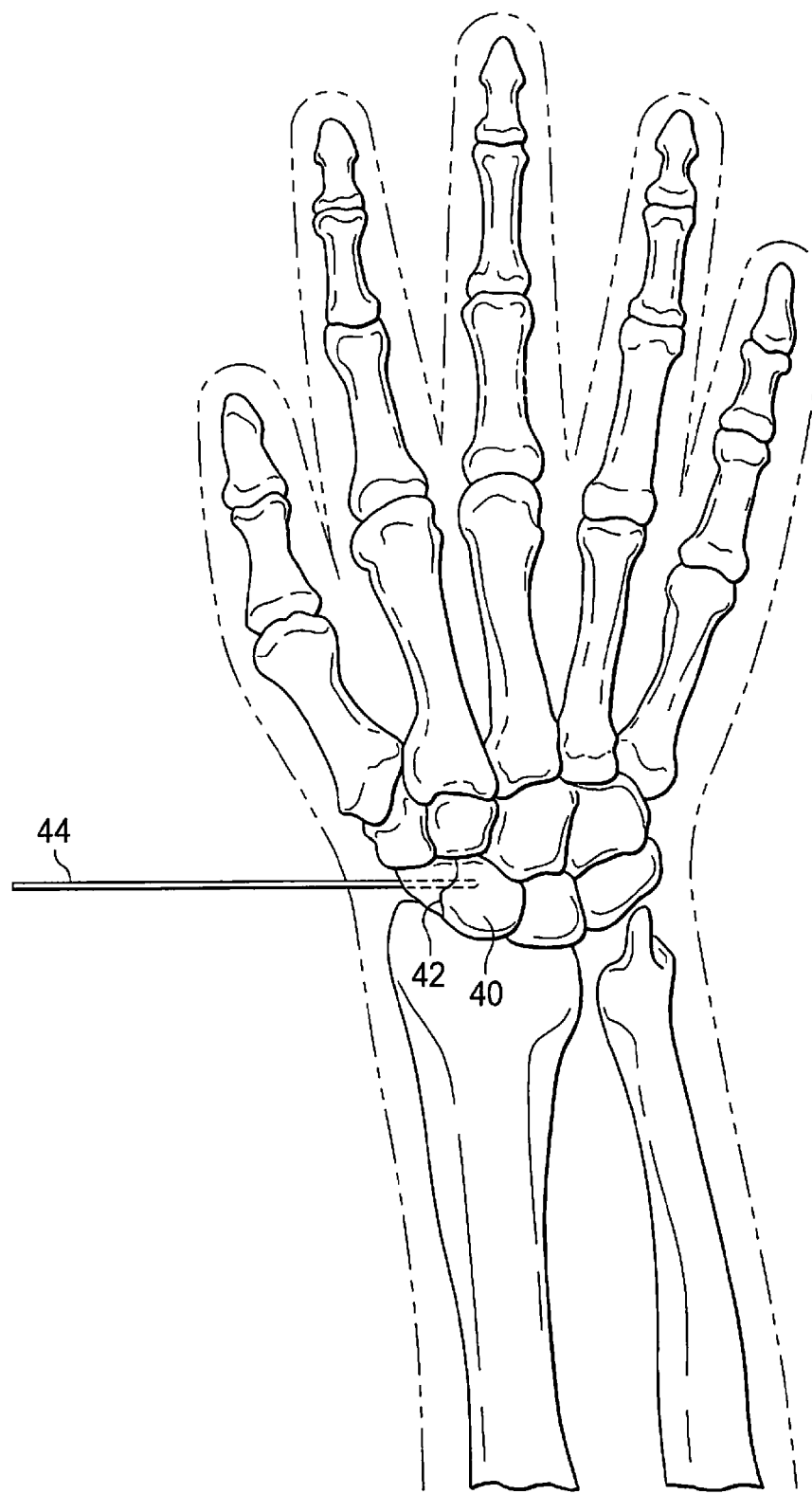
FIGS. 2A-D disclose the conventional technique for installation of a cannulated screw.

In FIG. 2A, for illustrative purposes only, scaphoid bone 40 of the right hand of a human is shown. The scaphoid bone 40 has been fractured along fracture line 42. The following procedure demonstrates problems associated with the conventional technique of attempting to install a cannulated screw to draw the fractured portions of the scaphoid bone 40 together to accelerate healing. Referring still to FIG. 2A, the surgeon makes an incision and directs a guide wire 44 into the scaphoid, transversing fracture 42. Guide wire 44 may be a well-known conventional guide wire, such as a Kirschner wire also known as a K-wire.

Figure 2B:
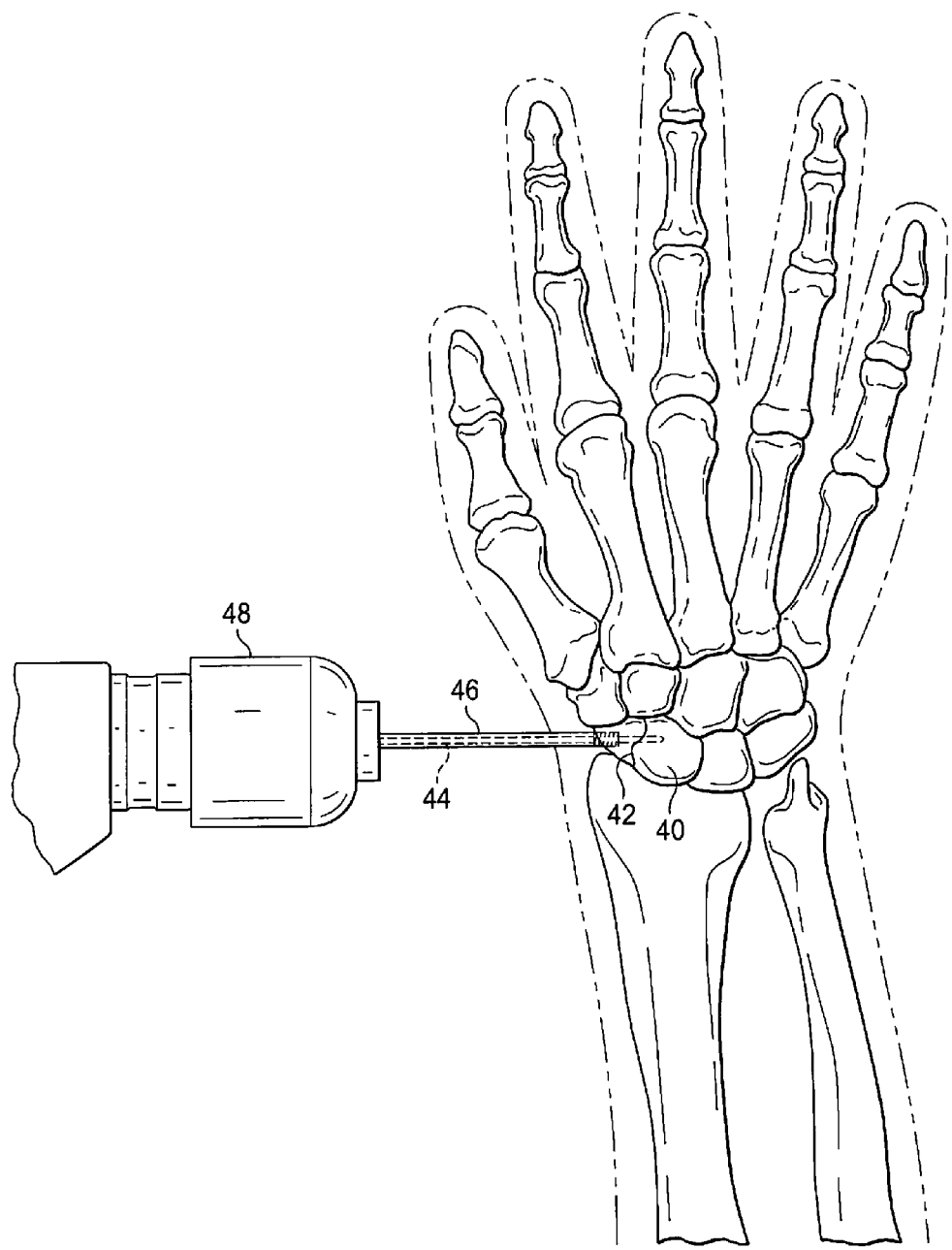

Referring now to FIG. 2B, once guide wire 44 is located in its final position, the surgeon will use a cannulated drill bit 46, which passes over guide wire 44 and drills a hole in a portion of scaphoid 40. In this manner guide wire 44 is being used to assist the surgeon in the proper orientation of drill bit 46. Preferably, drill bit 46 is only drilled approximately 3 mm-5 mm, or preferably maybe no more than about ¼ to ⅓$^{rd}$ of the depth of guide wire 44 in order to bridge the fracture so that the cannulated screw once installed would bridge the fracture. Obviously, such a depth would depend on where the fracture is but such is provided to provide one skilled in the art with relative depths.

Figure 2C:
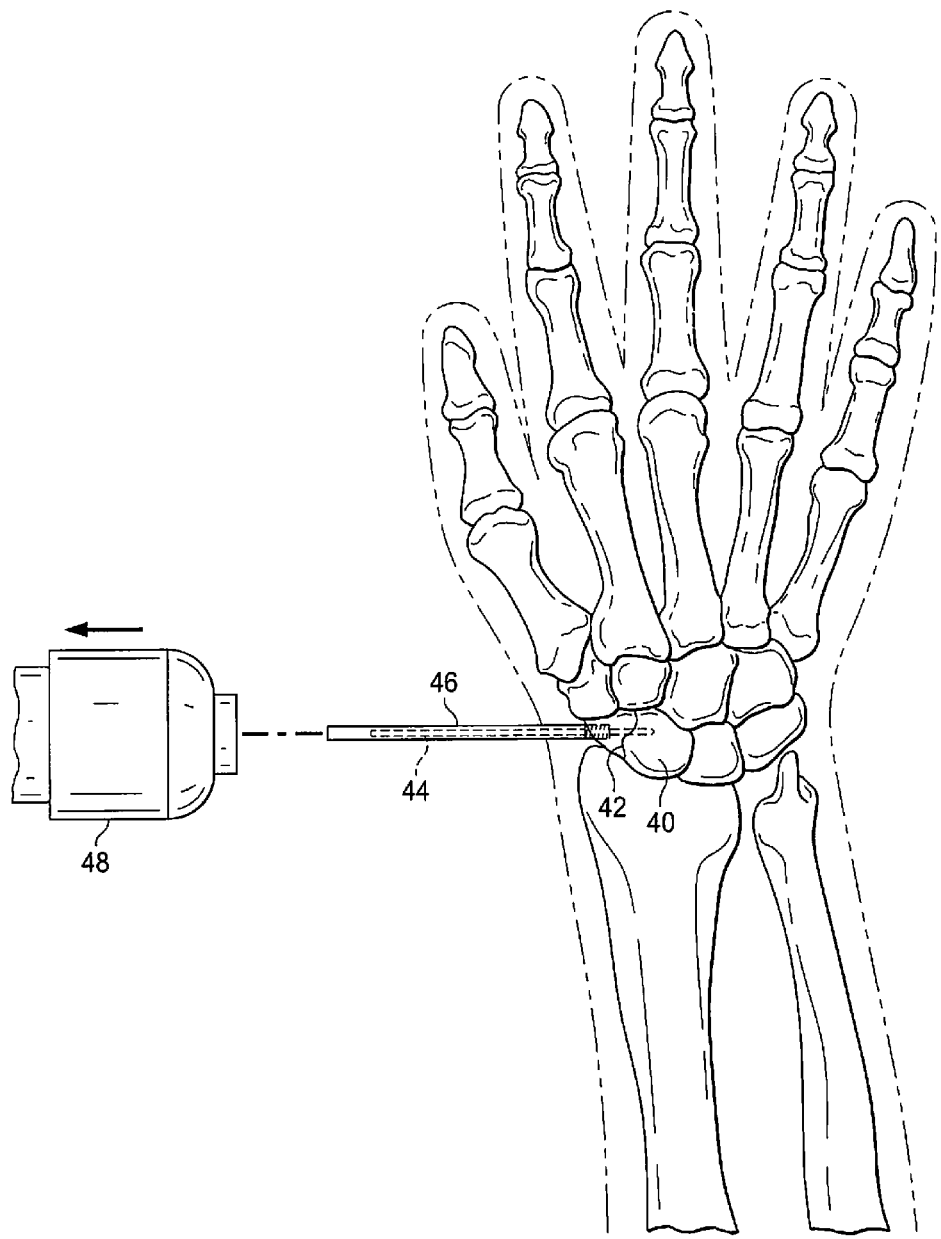
Figure 2D:
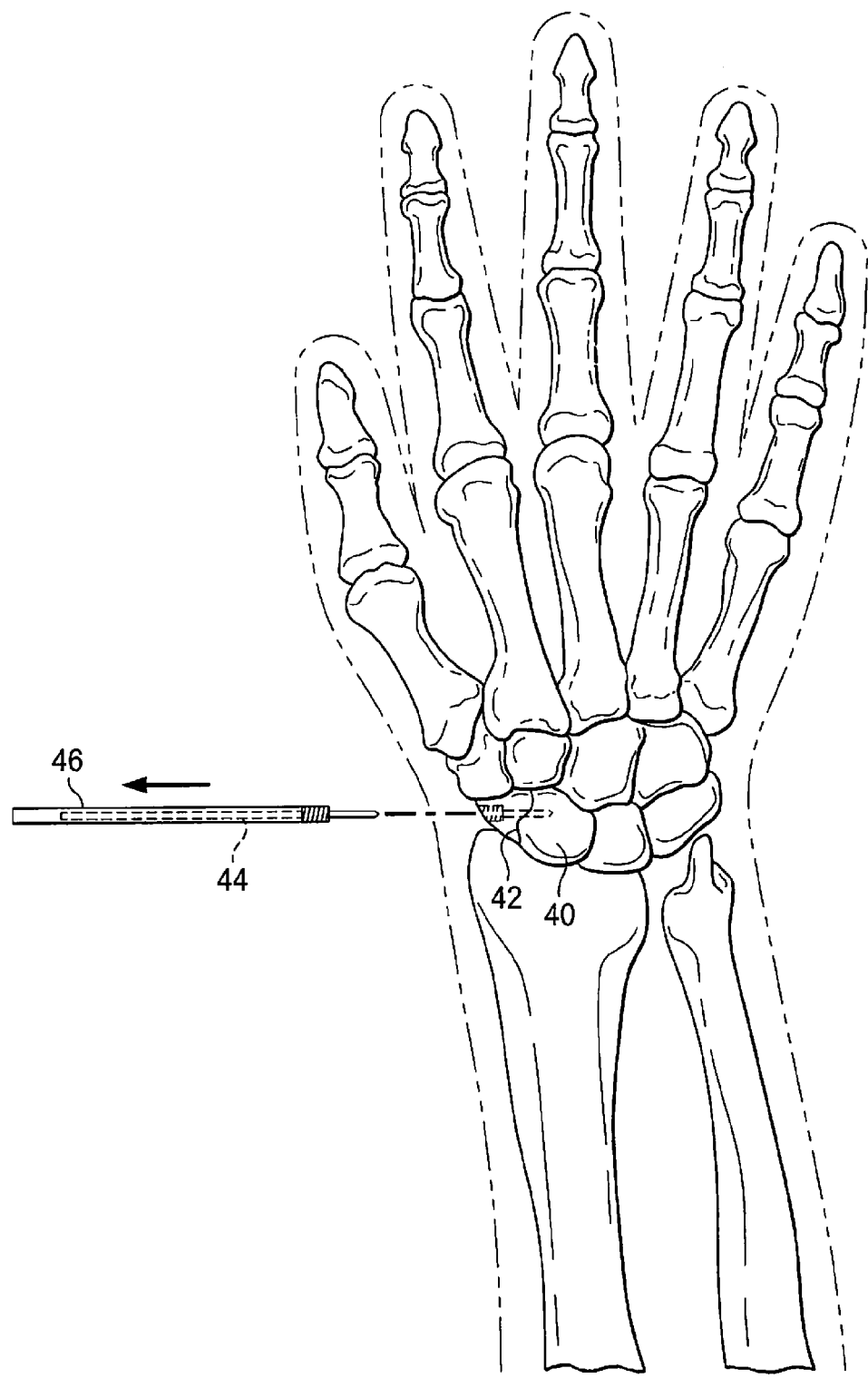

Referring now to FIG. 2C, drill 48 has been disconnected from drill bit 46. After doing so, the surgeon would unthread drill bit 46, leaving the larger threaded portion 48 created by drill bit 46 in the bone and, at the same time, leaving guide wire 44 in the bone to act as a future guide for lowering the cannulated screw and directing it toward the fracture line 42. However, in attempting to remove drill bit 46, it occasionally binds with guide wire 44 and, in removing drill bit 46, guide wire 44 is also inadvertently removed as shown in FIG. 2D. The results in loss of access to the target site on the bone. The surgeon then finds himself in the position of having to search through the soft tissue and try to rediscover the target site in the threaded connections. This can significantly irate the wound, is time-consuming and results in loss of the precise three-dimensional orientation of the drill site made within the bone, in this case scaphoid 40.

Referring now to FIGS. 3A-3J, the improved surgical procedure of the present invention will be described in conjunction with the use of the percutaneous exchange tube 10 as shown in FIG. 1.

Figure 3A:
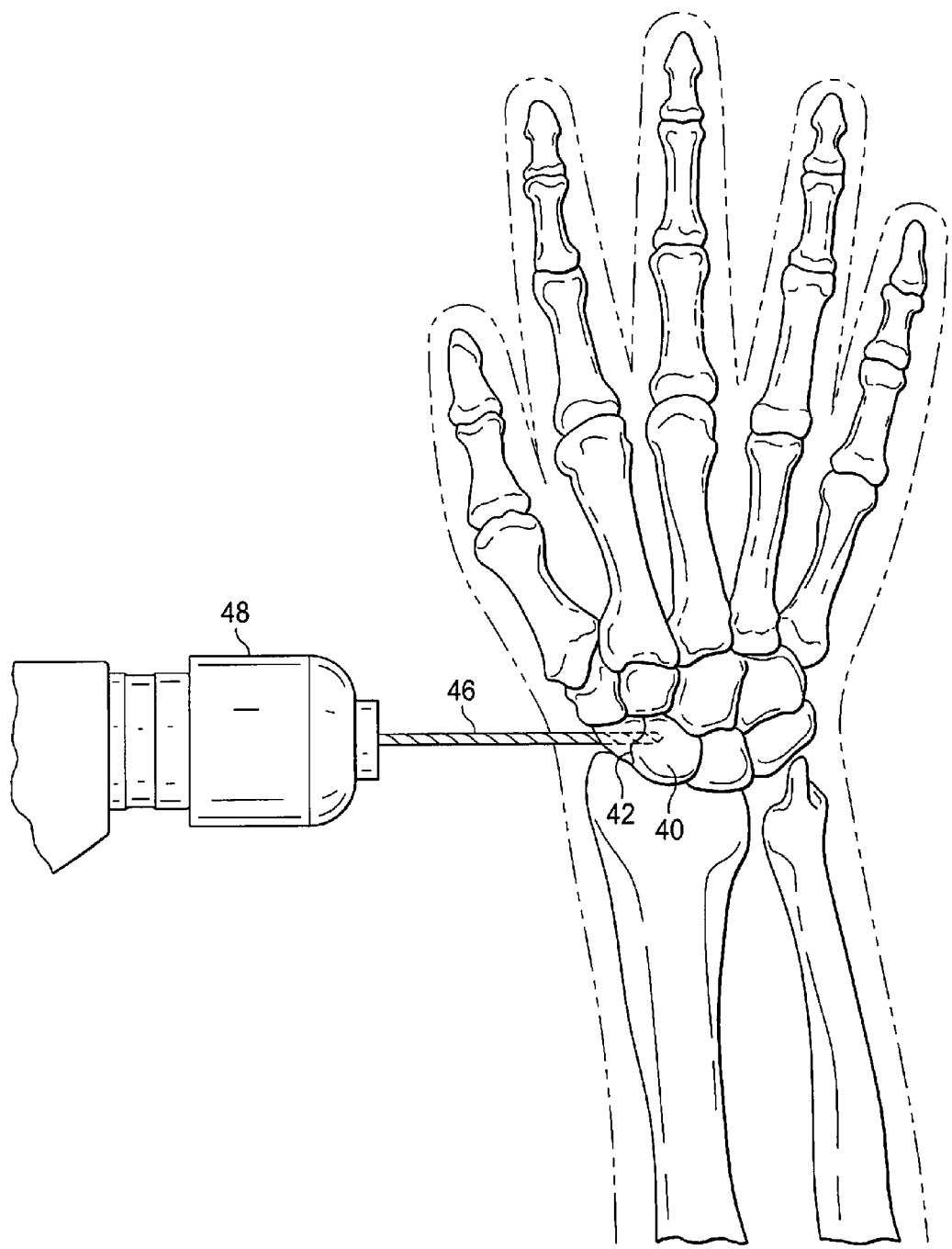
FIGS. 3A-J illustrate the inventive method of the present invention.
Figure 3B:
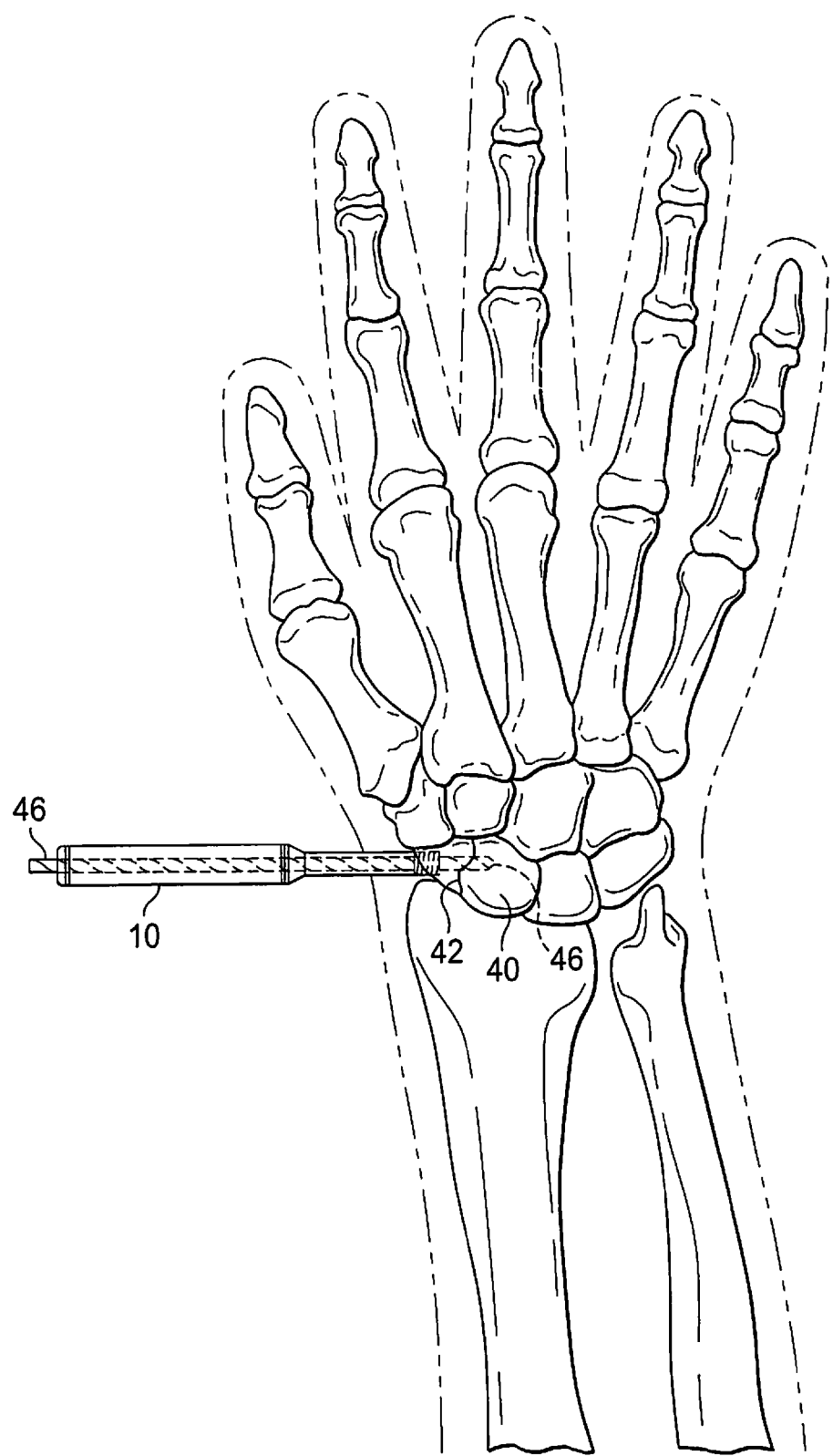

Referring to FIG. 3A, the preferred procedure is, in fact, counterintuitive compared to the conventional procedure shown in FIGS. 2A-2D. That is, in FIG. 3A, the surgeon first uses a drill 48, which is again attached to drill bit 46, to drill the first incision into scaphoid 40 in an effort to draw together fracture line 42. As in the case of the conventional technique, drill bit 46 is larger in diameter than guide wire 44. The surgeon uses drill 48 to orient bit 46 into scaphoid 40, transecting fracture line 42. Thus, while drill bit 46 may be the same size as used in FIG. 2C, it serves as the initial guide. Once drill bit 46 drills past fracture line 42 within scaphoid 40 a sufficient depth, drill 48 is disconnected. At that point, the surgeon places the threaded portion 24 of exchange tube 10 over drill bit 46 and lowers exchange tube 10 using drill bit 46 as the guide as shown in FIG. 3B. Since first end 16 of first portion 12 of exchange tube 10 includes the threaded portion 24, the surgeon then screws exchange tube 10 into the scaphoid bone 40. Threaded portion 24 is preferably about 3 mm -8 mm in length, more preferably about 4 mm-6 mm in length and most preferably about 5 mm in length. Preferably, drill bit 46 is drilled into the scaphoid 40 approximately two to three times the length of threaded portion 46. In this manner, exchange tube 10 is anchored within scaphoid bone 40.

Figure 3C:
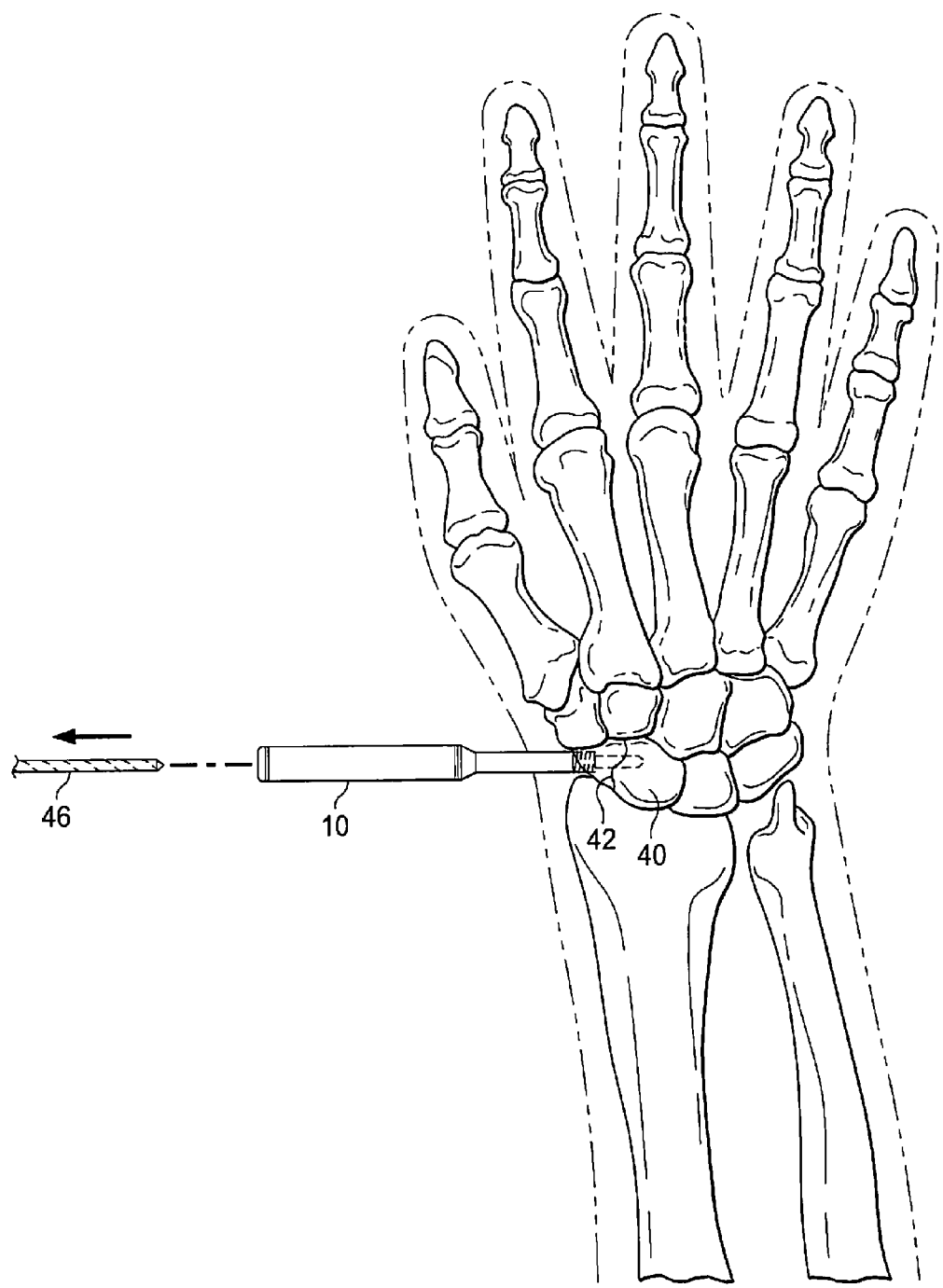

Referring now to FIG. 3C, after exchange tube 10 is anchored within scaphoid bone 40, drill bit 46 is unthreaded and removed. This leaves exchange tube 10 extending out from the target site and providing an open conduit through hollow, elongated portions 26 and 28.

Figure 3D:
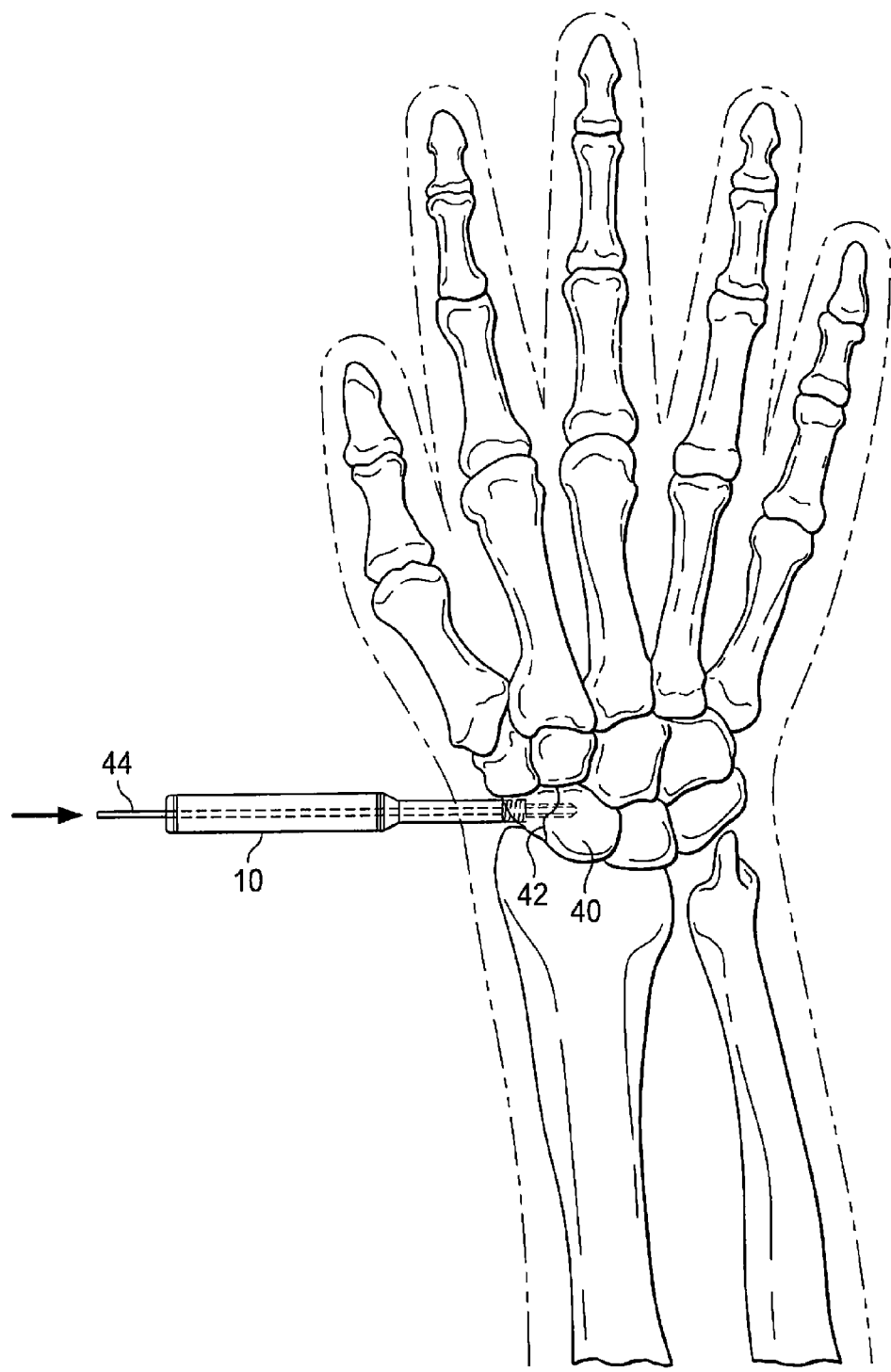

Referring now to FIG. 3D, a guide wire 44, which may be the same size guide wire as used in the conventional technique referred to in FIG. 2A, is then lowered through the hollow, elongated portions 26 and 28 of exchange tube 10 into scaphoid bone 40 where drill bit 46 had been previously. The outer diameter of guide wire 42 is less than the inner diameter of drill bit 46; however, guide wire 42 will center itself within the target site of scaphoid 40 previously drilled by bit 46. Typically, guide wire 42 has an outer diameter of approximately 0.8 mm-1.2 mm, whereas the inner diameter of drill bit 46 is typically 0.1 mm larger than the outer diameter of the guide wire. Typically, drill bit 46 would have an outer diameter of approximately 1.8 mm-2.6 mm.

Figure 3E:
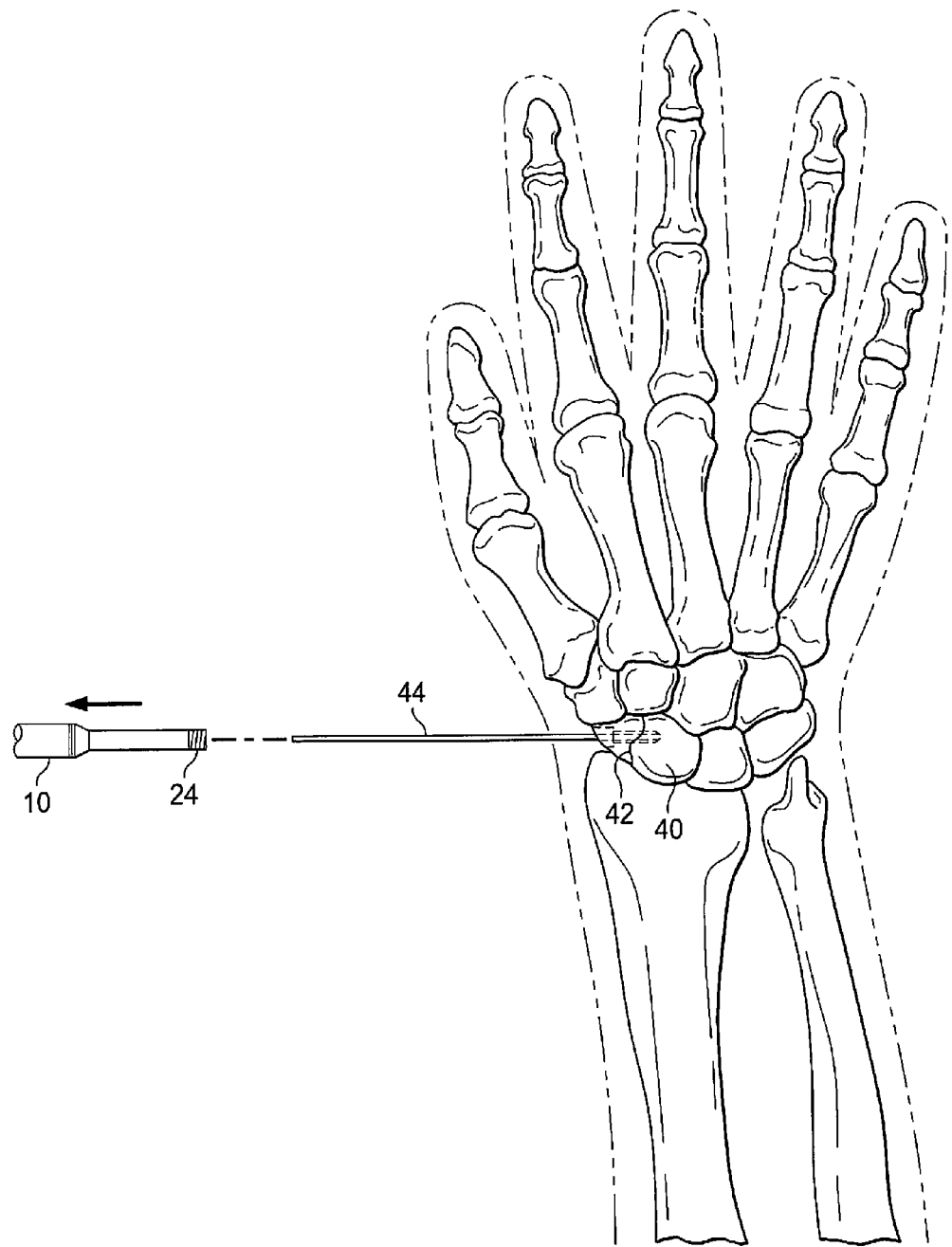

Referring now to FIG. 3E, once guide wire 44 is located within the drilled portion of scaphoid bone 40 as discussed above, exchange tube 10 is unscrewed at threaded connection 24 and removed. Due to the increased diameter of the hollow portions 26 and 28 compared to the outer diameter of the guide wire 44, the surgeon can easily remove exchange tube 10 without interference or otherwise accidentally removing guide wire 44. This is a substantial improvement over the conventional technique and is counterintuitive to the traditional practices that a surgeon would follow. That is, the present inventive method teaches that the surgeon first use a larger guide (drill bit 46) to create the initial hole and then, through the use of exchange tube 10 acting as a guide due to anchored threaded portion 24, insert a traditional guide wire 44 through exchange tube 10 into the drilled site within the bone.

Figure 3F:
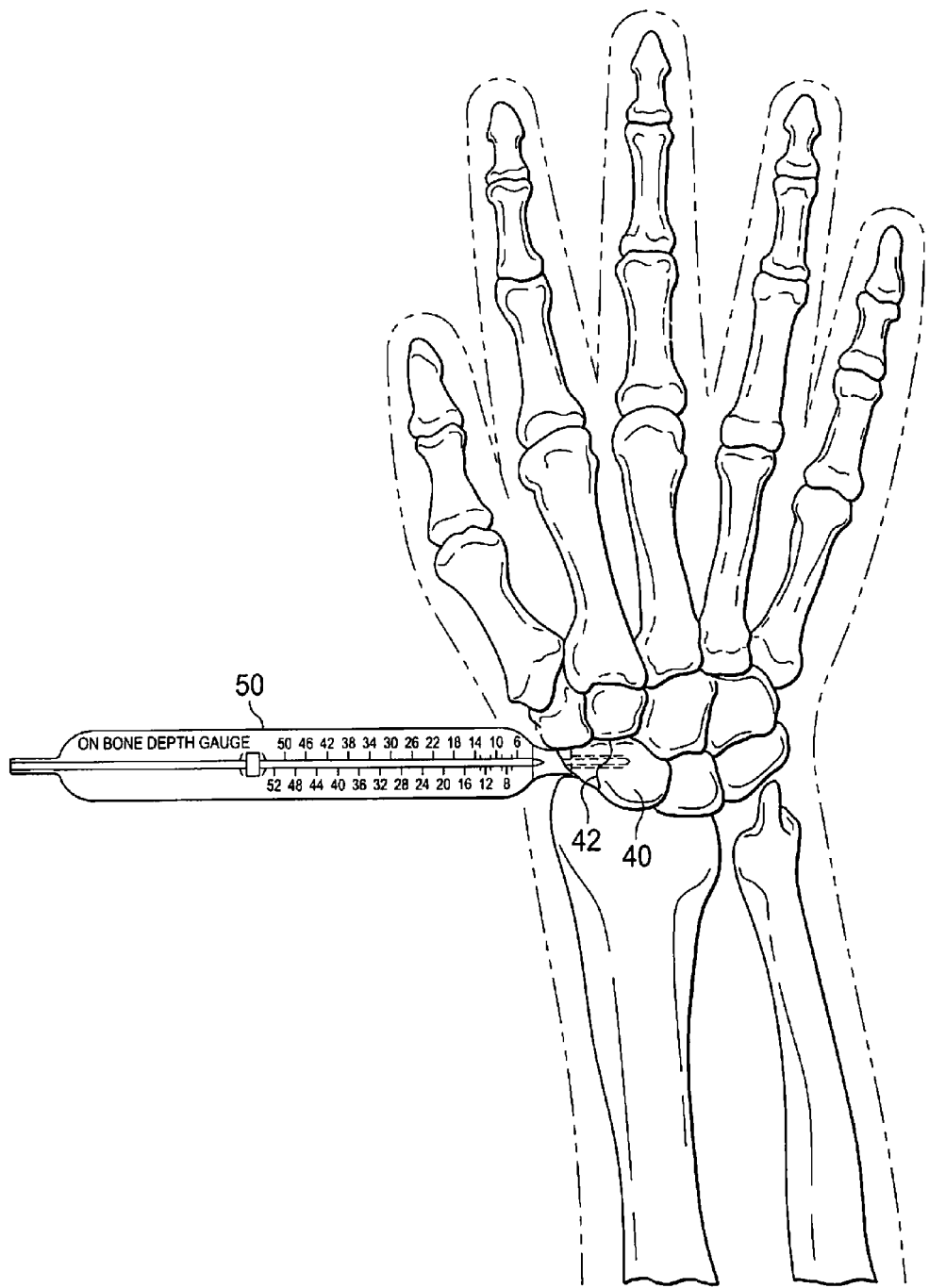

Referring now to FIG. 3F, it may be desirable for the surgeon to take a measurement of the depth of the drilled hole so that a cannulated screw of the correct length may be selected. To do this a conventional measuring device 50 is placed against the top of the scaphoid 40 and a measurement of the depth of the drilled hole is taken using a conventional device 50. Such a device 50 may be, for example, model 316-0135, entitled HPS Dual Cannulated Depth Gage available through OsteoMed, LLC, of Addison, Tex. Once the measurement of the depth of the drilled site is made and the correct cannulated screw selected, the installation of the cannulated screw begins.

Figure 3G:
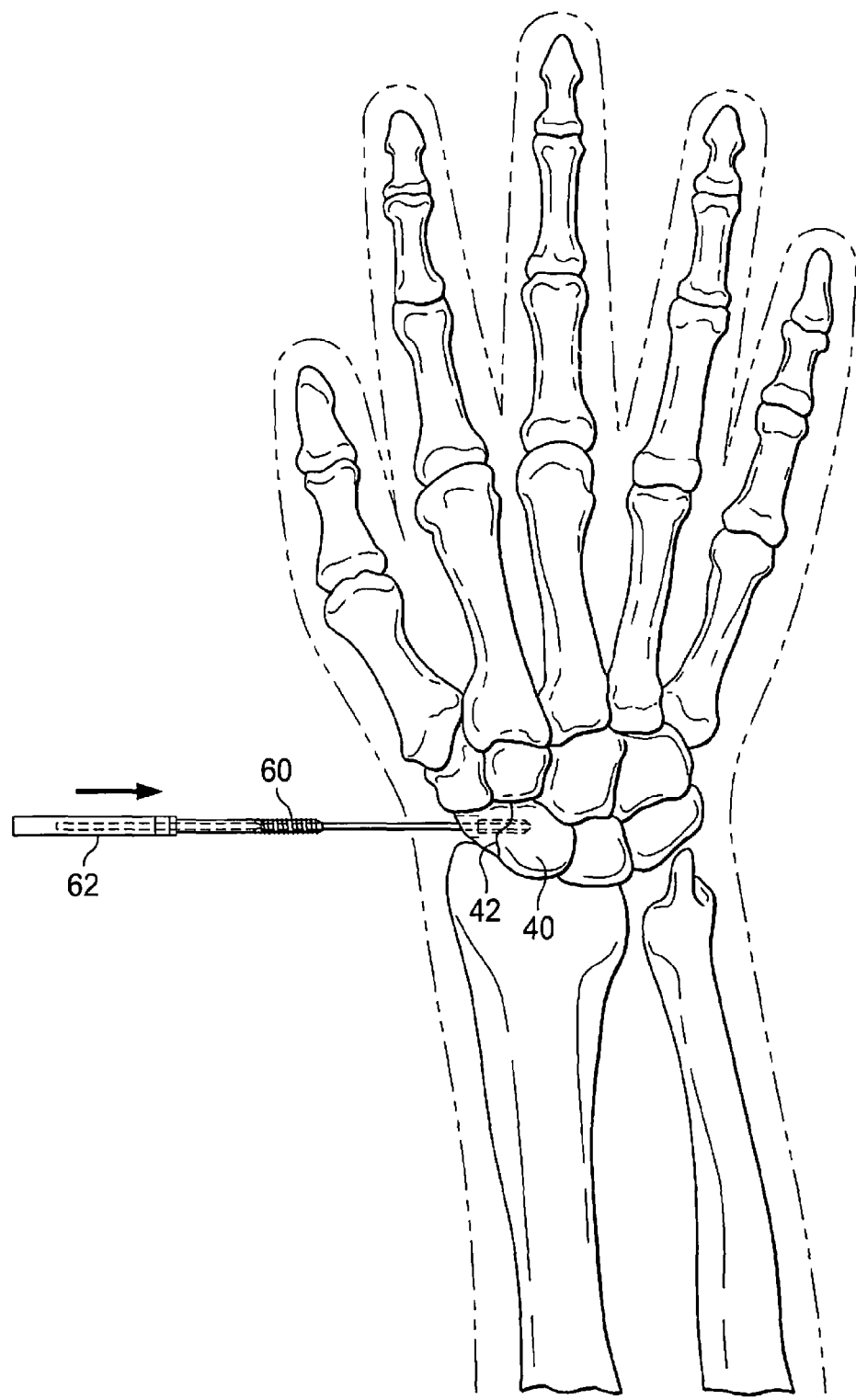

Referring now to FIG. 3G, cannulated screw 60 is placed over guide wire 44. Additionally, cannulated screwdriver 62 is then placed over guide wire 44 and both are lowered down the guide wire into the wound and positioned at the target site as shown in FIGS. 3G and 3H.

Figure 3H:
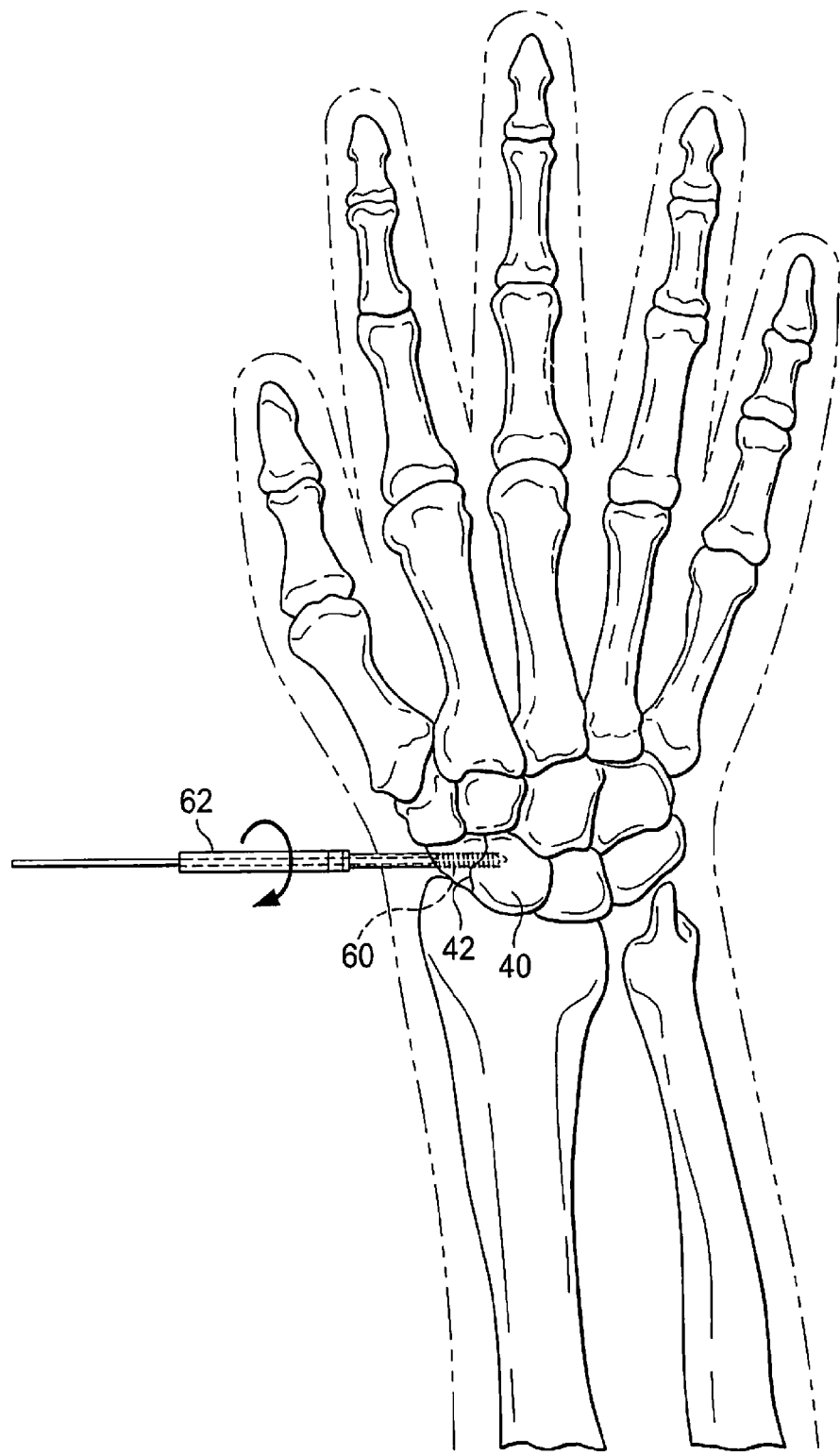

Referring now to FIG. 3H, screwdriver 62 is rotated, threading cannulated screw 60 across fracture line 42 within scaphoid 40. Cannulated screw 60 is a conventional cannulated headed or headless screw, such as models 319-2420 and 317-2420, available from OsteoMed, LLC, of Addison, Tex. Similarly, cannulated screwdriver 62 is well-known to those skilled in the art, e.g., model 316-0132 or 316-0304, available from OsteoMed, LLC, of Addison, Tex. Screwdriver 62 may include any number of drive arrangements that mate with the drivable end of cannulated screw 60. For example, such may be of a hex configuration or other shaped driving arrangement well known to those skilled in the art.

Figure 3I:
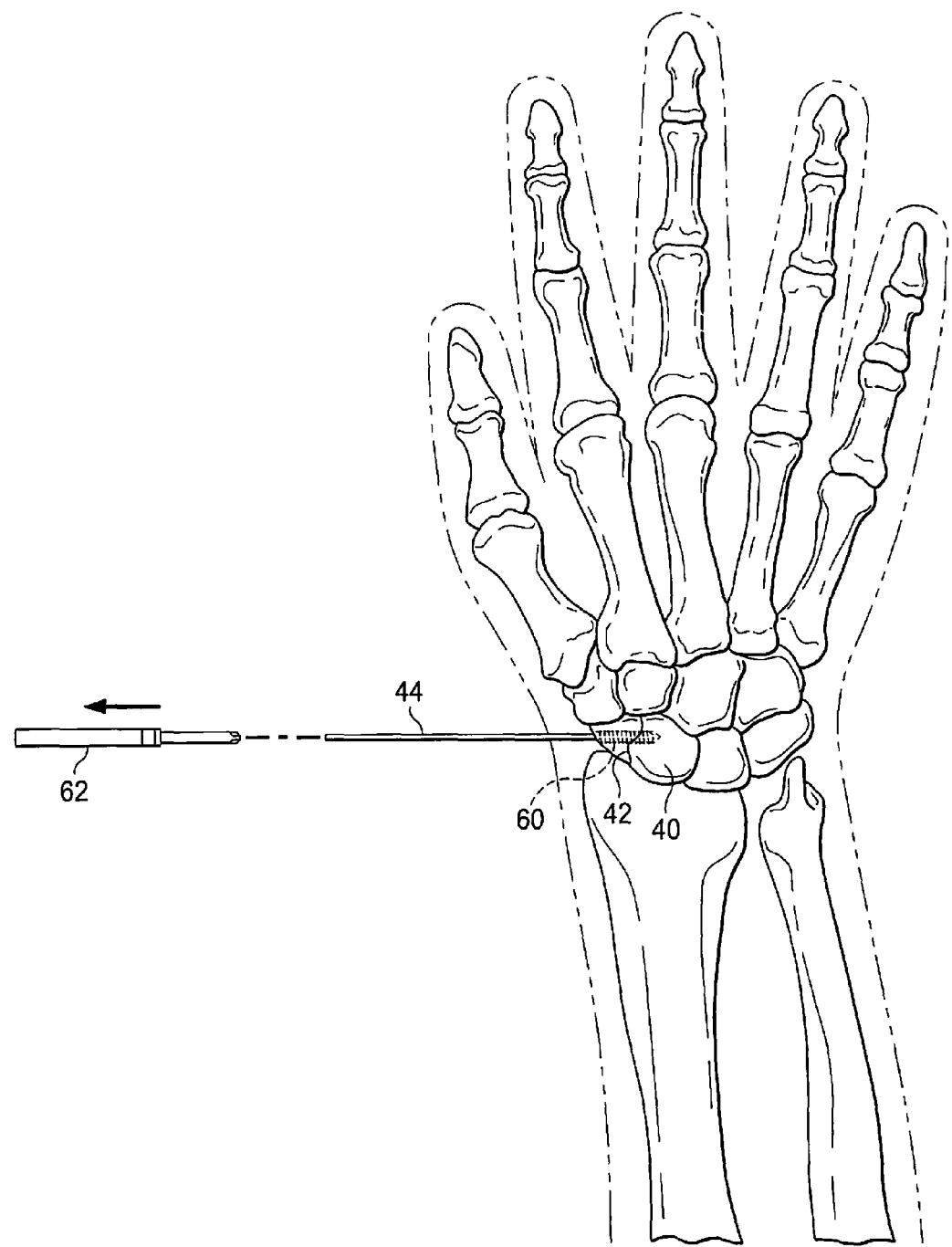
Figure 3J:
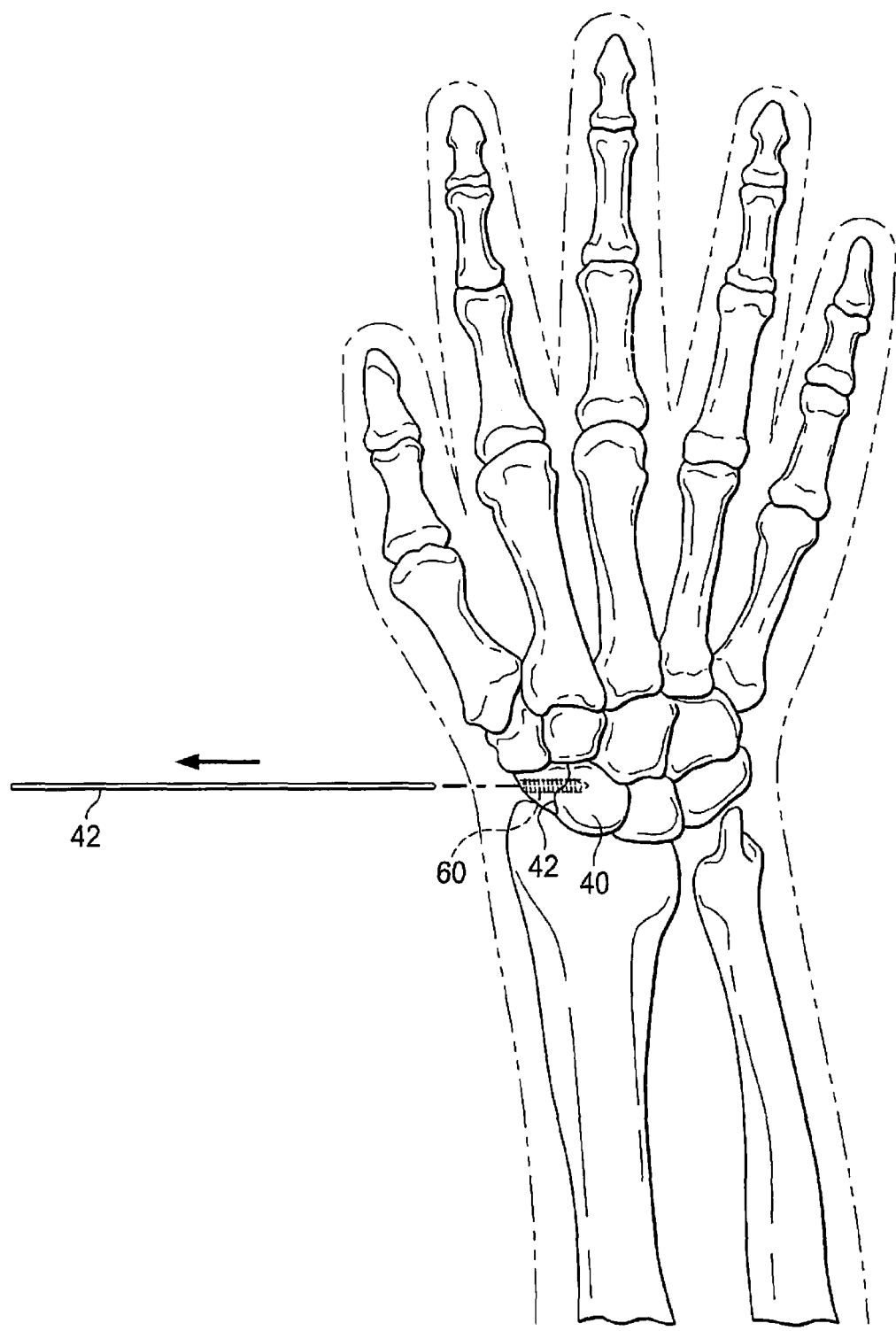

Once the cannulated screw is located to its final position spanning the fracture 42, screwdriver 62 is removed as shown in FIG. 3I, leaving cannulated screw 60 in its final position. At that point, the surgeon need only remove guide wire 42, as shown in FIG. 3J, and close up the wound.

The improved medical procedure, as outlined above with respect to FIGS. 3A-3J, is possible as a result of the design and use of percutaneous exchange tube 10 which provides for an additional anchoring and guiding mechanism as described above. It will be apparent to one of ordinary skill in the art that the improved procedure of the present invention is unorthodox in that it reverses the typical sequence of first placing a guide wire 44 that is then followed by the use of a drill bit 46 placed over guide wire 44. That is, the present invention teaches the use of a later drill bit 46 first to drill the site and use that bit as a first guide. This is possible because of the design and use of exchange tube 10 that provides a system to secure an open, aligned and oriented field once the drill bit 46 is removed and for the subsequent placement of a conventional guide wire 44 in accordance with the description set forth above.

The present invention has been described in terms of a fracture of the scaphoid bone of the human hand. However, the present invention may be used in a surgical procedure on any bone of the human bone that has been fractured. Additionally, the cannulated screws discussed with respect to the present invention may be used in attaching fixation plates across a fracture or portion of a human bone in need of assistance from a fixation place. Such a fixation plate may be that as shown as models 333-2401, 333-2403, 336-2772 and described in OsteoMed's brochures at its website www.osteoMed.com. Furthermore, the cannulated screw may be of a headless or headed version. The headed version may be a hex drive arrangement or any other connection mating arrangement well known to those skilled in the art. If a headed cannulated screw is used an intermediate drilling step would be included preferably either before or after the measurement of the depth of the drill site is made as shown in FIG. 3F. Such a countersink drilling step is very limited in depth and is made to accommodate the increased diameter of the head of the cannulated screw. Such a countersink drilling step is well known to those skilled in the art.

Exchange tube 10 may be manufactured of any suitable material for use in human surgical procedures such as 17-4 PH stainless steel.

Although the embodiments of the present disclosure and their advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A method for installation of a screw within a human bone, said method comprising the steps of:
   providing an installation tube having;
      a first elongated hollow portion having a first and second end, said first end being threaded, and
      a second elongated hollow portion having a first and second end, said first end of said second elongated portion being attached to said second end of said first elongated portion,
      wherein said first elongated hollow portion is co-axially aligned with said second elongated hollow portion and the inner diameter of said first elongated hollow portion is substantially the same as the inner diameter of the said second elongated hollow portion;
   inserting a first guide wire into a target location of a human bone;
   placing the first end of the first hollow portion of the tube over the first guide wire;
   lowering the tube along the first guide wire;
   connecting the first end of the first hollow portion of the tube into the bone;
   removing the first guide wire;
   inserting a second guide wire having an outer diameter smaller than the outer diameter of the first guide wire through the elongated hollow portions of the tube and into the target location of the bone;
   disconnecting the tube and removing the tube, leaving the second guide wire within the target location of the bone;
   lowering a threaded cannulated screw over the second guide wire into the target location of the bone, the screw having a maximum threaded outer diameter greater than the outer diameter of the first guide wire and the outer diameter of the threaded end of the first elongated hollow portion of the tube;
   rotating the screw into the bone at the target location, fixing the screw in the bone; and
   removing the second guide wire.

2. The method according to claim 1, wherein said first guide wire is a Kirschner wire.

3. The method according to claim 1, wherein said method further comprises the step of measuring for a length of the cannulated screw.

4. The method according to claim 3, wherein said measuring step occurs after removal of the tube.

5. The method according to claim 1, wherein said first guide wire is inserted by drilling said first guide wire into the target location of the human bone.

6. A method for installation of a screw within a human bone, said method comprising the steps of:
   providing an installation tube having;
      a first elongated hollow portion having a first and second end, said first end being threaded, and
      a second elongated hollow portion having a first and second end, said first end of said second elongated portion being attached to said second end of said first elongated portion,
      wherein said first elongated hollow portion is co-axially aligned with said second elongated hollow portion and the inner diameter of said first elongated hollow portion is substantially the same as the inner diameter of the said second elongated hollow portion;
   inserting a first guide wire into a target location of a human bone;
   placing the first end of the first hollow portion of the tube over the first guide wire;
   lowering the tube along the first guide wire;
   threading the first end of the first hollow portion of the tube into the bone;
   removing the first guide wire;
   inserting a second guide wire having an outer diameter smaller than the outer diameter of the first guide wire through the elongated hollow portions of the tube and into the target location of the bone;
   unthreading the tube and removing the tube, leaving the second guide wire within the target location of the bone;
   measuring for a length of a threaded cannulated screw;
   lowering the cannulated screw over the second guide wire into the target location of the bone, the screw having a maximum threaded outer diameter greater than the outer diameter of the first guide wire and the outer diameter of the threaded end of the first elongated hollow portion of the tube;
   rotating the screw into the bone at the target location, fixing the screw in the bone; and
   removing the second guide wire.

7. The method according to claim 6, wherein said first guide wire is a Kirschner wire.

8. The method according to claim 6, wherein said measuring step occurs after removal of the tube.

9. The method according to claim 6, wherein said first guide wire is inserted by drilling said first guide wire into the target location of the human bone.

* * * * *